US012629475B2

(12) United States Patent
Zolotukhin

(10) Patent No.: US 12,629,475 B2
(45) Date of Patent: May 19, 2026

(54) INJECTION DEVICE AND COMPONENTS THEREOF

(71) Applicant: PULSE NEEDLEFREE SYSTEMS, INC., Lenexa, KS (US)

(72) Inventor: Mikhail Zolotukhin, Shawnee, KS (US)

(73) Assignee: PULSE NEEDLEFREE SYSTEMS, LLC, Lenexa, KS (US)

( * ) Notice: Subject to any disclaimer, the term of this patent is extended or adjusted under 35 U.S.C. 154(b) by 821 days.

(21) Appl. No.: 17/925,065

(22) PCT Filed: May 22, 2020

(86) PCT No.: PCT/US2020/034118
§ 371 (c)(1),
(2) Date: Nov. 14, 2022

(87) PCT Pub. No.: WO2021/236092
PCT Pub. Date: Nov. 25, 2021

(65) Prior Publication Data
US 2023/0181833 A1 Jun. 15, 2023

(51) Int. Cl.
*A61M 5/31* (2006.01)
*A61M 5/315* (2006.01)

(52) U.S. Cl.
CPC ........... *A61M 5/31* (2013.01); *A61M 5/31533* (2013.01)

(58) Field of Classification Search
CPC ................ A61M 5/31; A61M 5/31553; A61M 2205/3584; A61M 2205/8212
See application file for complete search history.

(56) References Cited

U.S. PATENT DOCUMENTS

| | | | |
|---|---|---|---|
| 3,425,413 A | 2/1969 | Stephens | |
| 3,859,996 A | 1/1975 | Mizzy et al. | |

(Continued)

FOREIGN PATENT DOCUMENTS

| | | |
|---|---|---|
| CN | 104399155 A | 3/2015 |
| WO | WO 2000/30704 A1 | 6/2000 |
| WO | 2003/068296 A2 | 8/2003 |

OTHER PUBLICATIONS

International Search Report and Written Opinion from related PCT/US2020/034118 dated Aug. 19, 2020 (15 pgs).

*Primary Examiner* — Dung T Ulsh
(74) *Attorney, Agent, or Firm* — STINSON LLP

(57) ABSTRACT

Disclosed are an injection device and a method of using the same. The injection device includes an injection drive assembly including a pneumatic piston chamber, dose chamber, pneumatic piston slidably positioned in the pneumatic piston chamber and an injectate piston slidably positioned in the dose chamber. The injection drive assembly is configured so that any energy resulting from an application of force to the injection drive assembly is instantaneously available for the initiation of injection. In another aspect, the injection device includes separate respective resilient members for each of the pistons that are configured to position each piston in their respective pre-injection positions. In still another aspect, the injection device includes a valve assembly configured to provide pressurized fluid to the pneumatic piston chamber. The rate of the movement of the valve between open and closed positions is independent of control by a user of the injection device.

21 Claims, 5 Drawing Sheets

(56)                    References Cited

U.S. PATENT DOCUMENTS

| | | | |
|---|---|---|---|
| 4,342,310 A | | 8/1982 | Lindmayer et al. |
| 4,623,332 A | | 11/1986 | Lindmayer et al. |
| 5,746,714 A | | 5/1998 | Salo et al. |
| 5,782,802 A | | 7/1998 | Landau |
| 6,203,521 B1 | | 3/2001 | Menne et al. |
| 6,585,698 B1 | * | 7/2003 | Packman ............... G16H 20/17 |
| | | | 604/207 |
| 6,676,630 B2 | | 1/2004 | Landau et al. |
| 6,770,054 B1 | | 8/2004 | Smolyarov et al. |
| 7,029,457 B2 | | 4/2006 | Rogatchev et al. |
| 7,291,132 B2 | * | 11/2007 | DeRuntz ........... A61M 5/31558 |
| | | | 604/207 |
| 7,357,781 B2 | | 4/2008 | Menassa |
| 7,442,182 B2 | | 10/2008 | Landau et al. |
| 9,662,460 B2 | | 5/2017 | Menassa |
| 2003/0088207 A1 | | 5/2003 | Rogatchev et al. |
| 2003/0225368 A1 | * | 12/2003 | Landau ................... A61M 5/30 |
| | | | 604/70 |

* cited by examiner

INJECTION DEVICE AND COMPONENTS THEREOF

BACKGROUND OF THE INVENTION

1. Field of the Invention

The present invention relates to the field of injection devices.

2. Description of Related Art

Injections of humans and animals are commonly performed by syringes with needles. Because the use of needles has numerous drawbacks, including pain, medical sharps waste, and the risk of disease transmission through needle re-use, needle-free injection is an emerging delivery method.

Needle-free injection devices commonly use a pneumatic piston (referred to as a power piston) slidably positioned in a pneumatic piston chamber to drive an injectate piston (referred to as a plunger or hydraulic piston) slidably positioned in a dose chamber forward to expel liquid through an orifice under pressure. The pneumatic piston slidably positioned in a pneumatic piston chamber and the injectate piston slidably positioned in the dose chamber are components of the injection drive assembly of an injection device. This process of pressurizing the liquid and expelling the liquid through an orifice generates a very narrow injection stream that can pierce human or animal tissues. Springs, magnets, locks, hydraulics and pneumatics are commonly used to propel a power piston and, in turn, a plunger or other medicine piston. In needle-free injectors, the power piston propulsion systems are important because it is desirable to generate a high initial pressure to the liquid to be expelled. This high initial pressure to the liquid helps the initial portion of the injection stream penetrate tissue and create an opening for the remaining portion of the injection stream to pass through that opening and enter the tissue. If the initial hydraulic pressure is insufficient, the initial portion of the injection stream may fail to penetrate the target tissue and prevent the full dose of the liquid from being injected, or the injection stream may otherwise fail to reach the desired injection depth, such as the subcutaneous or intramuscular tissue layers.

Because the initial hydraulic pressure is determined by the speed at which the power piston and medicine piston move, injection devices commonly include an energy accumulator. As used herein, the term "energy accumulator" means a device or component of an injection drive assembly that is configured to store potential energy (for example, in the form of a stored pressurized fluid) until the stored potential energy reaches a predetermined threshold prior to making any energy available for the initiation of an injection cycle. As used herein, the term "injection cycle" means the movement of an injection drive assembly from the pre-injection position, to the post-injection position, and back to the pre-injection position. An energy accumulator enables the power piston to accelerate rapidly at the initiation of an injection cycle. For example, a spring may be attached to the power piston, and the spring may be compressed and retained such that, once the spring is released, the power piston travels rapidly forward with an initial impulse of energy. One limitation of energy accumulators is that they require additional components to store the potential energy and to retain or lock the power piston in the pre-injection position until the stored energy is released. Additionally, the operation of energy accumulators results in additional wear and tear on the power piston and any components that retain or lock the power piston in the pre-injection position until the stored energy is released. In the spring example described above, during the time in which the spring is compressed but not yet released, there will be wear and tear on the spring and the power piston. Also, the clamp or other retention mechanism that holds the spring in the compressed position and/or retains or locks the power piston until the stored energy is released will wear over time. Similar limitations are present in other energy accumulators, including magnets, locks, hydraulics and pneumatics.

It is also common in the art to attach the power piston to the medicine piston so that movement of one of these pistons will also move the other piston. This attachment of the power piston to the medicine piston allows both pistons to move forward in unison at the beginning or actuation of the injection cycle. Similarly, when preparing the injector for the injection, because the power piston and hydraulic piston are attached to each other, it is only necessary to apply force to one of the pistons to achieve the movement of both of the pistons. However, the attachment of the power piston to the medicine piston does have drawbacks. For example, the forward or distal movement of the power piston is encumbered by the power piston's attachment to the medicine piston, as the medicine piston creates additional drag. In many applications, this encumbrance on the movement of the power piston does not prevent the power piston and medicine piston from generating a sufficient impulse to deliver an injection. However, in some high-workload and/or high-pressure applications such as injecting large animals, anything that encumbers the forward movement of the power piston can require that greater energy be used to deliver the injection, or otherwise negatively affect injection quality.

One example of an injection device that includes an energy accumulator and a power piston that is attached to the medicine piston is shown and described in U.S. Pat. No. 6,770,054 (the "'054 Patent"). The '054 Patent is incorporated by reference herein in its entirety. The injection device disclosed in the '054 Patent includes a ball lock assembly that is locked and then released (unlocked) in order to drive a power piston in the distal direction, which in turn drives the distal movement of a medicine/hydraulic piston that is attached to the power piston. This distal movement of the medicine piston expels medication from the device. The ball lock assembly is releasable from the locked position to drive the power piston forward when a predetermined amount of pneumatic pressure is achieved within the pneumatic piston chamber or cylinder. Thus, at least the ball lock assembly functions as an energy accumulator, and more specifically, as a pressurized fluid accumulator. The power piston is held in the pre-injection position by the ball lock assembly until a predetermined amount of pneumatic pressure is achieved within the pneumatic piston chamber. As is also described in the '054 Patent, the power piston and medicine piston are a single, unified component such that movement of the power piston necessarily moves the medicine piston.

Another example of an injection device that includes an energy accumulator and a power piston that is attached to the medicine piston is shown and described in U.S. Pat. No. 5,782,802 (the "'802 Patent"). The injection device disclosed in the '802 Patent includes a ball lock assembly that is locked and then released (unlocked) in order to drive a power piston in the distal direction, which in turn drives the distal movement of a medicine piston that is attached to the power piston. This distal movement of the medicine piston expels medication from the device. The ball lock assembly is releasable from the locked position to drive the power piston forward when a mechanical spring is cocked and in the locked position. Thus, at least the ball lock assembly functions as an energy accumulator. The power piston is held in the pre-injection position until the power piston is released by the operator pressing the injection button. Additionally, the piston tip (medicine piston) is firmly mounted on the ram tip, which is integral part of the ram (power piston). Thus, distal and proximal movement of the ram (power piston) in turn moves the piston tip (medicine piston) distally and proximally.

Yet another example of an injection device that includes an energy accumulator and a power piston that is attached to the medicine piston is shown and described in U.S. Pat. No. 7,357,781 (the "'781 Patent"). The injection device disclosed in the '781 Patent includes a magnetic lock assembly that is locked and then released (unlocked) in order to drive a piston (power piston) in the distal direction, which in turn drives the distal movement of a plunger (medicine piston) that is attached to the power piston via a coupler. This distal movement of the plunger (medicine piston) expels medication from the device. The magnet lock assembly is releasable from the locked position to drive the piston (power piston) forward when a predetermined amount of pneumatic pressure is achieved. The trigger is pressed manually in order to open the on/off gas valve. Once the on/off gas valve is opened, pressurized gas flows into a pressure chamber located behind the power piston. When gas pressure in the pressure chamber overcomes the force of the magnet lock, it propels the piston (power piston) and plunger (medicine piston) forward to discharge the liquid via an orifice. Thus, at least the pressure chamber and the magnetic lock assembly function as pressurized fluid accumulators. The power piston is held by the magnetic lock assembly in the pre-injection position until a predetermined amount of pneumatic pressure is achieved within the pressure chamber. Additionally, the plunger (medicine piston) is firmly mounted to a coupler, which is slidably attached to the piston (power piston) via a retractor (part of the power piston assembly). Thus, the medicine piston and the power piston are indirectly attached to one another, and as a result, the distal and proximal movement of the piston (power piston) in turn moves the plunger (medicine piston) distally and proximally.

Another example of an injection device that includes an energy accumulator and a power piston that is attached to the medicine piston is shown and described in U.S. Pat. No. 6,676,630 (the "'630 Patent"). The injection device disclosed in the '630 Patent includes a gas reservoir (a pressure accumulation chamber) that is separated from a piston chamber by a poppet valve. The poppet valve may be released (unlocked) in order to supply high pressure gas from the pressure accumulation chamber to the piston chamber which contains the piston (power piston) and plunger (medicine piston). Gas supplied from the gas reservoir to the piston chamber drives the piston (power piston) in the distal direction, which in turn drives the distal movement of a plunger (medicine piston) that is in abutting contact with the power piston. This distal movement of the plunger (medicine piston) expels medication from the device. The poppet valve is releasable from the closed or locked position to supply high pressure gas to the piston chamber to drive the piston (power piston) forward when a predetermined amount of pneumatic pressure is achieved in the gas reservoir. Thus, at least the gas reservoir functions as an energy accumulator. Once the predetermined amount of pressure is achieved in the gas reservoir, a burst of power/pressure is provided to the power piston. Additionally, the plunger (medicine piston) is attached to the piston (power piston) and retained by a spring (return spring). Thus, distal movement of the piston (power piston) in turn moves the plunger distally, and proximal movement of the plunger (medicine piston) in turn moves the piston (power piston) proximally.

Although the injection devices described above function as intended, there are certain drawbacks associated with these designs including but not limited to the following. First, all of the referenced injectors include components that function as energy accumulators. While the utilization of energy accumulators in injection devices enables the rapid movement of the power piston in order to obtain a high quality injection profile, energy accumulators are frequently the failure point of many injectors. This is because energy accumulators store potential energy, subjecting them to significant strain and wear. This increases the service frequency, as components that function as energy accumulators must be serviced or replaced. For example, magnets, springs, locks and valves that function as energy accumulators will wear out over time and subsequently not work as intended.

Second, the injection devices described above are prone to delivering inconsistent injections as a result of the fact that the operation of the valves which provide pressurized gas to the injection drive assemblies may be impacted by human error and/or fatigue. For example, with regard to those injection devices that require an operator to depress a button to open a valve in order to provide pressurized fluid to the injection drive assemblies, the force with which the operator depresses the button can affect the rate at which the valve moves from the closed to the open position and/or whether the valve is only partially opened; this in turn can affect gas feed rate. For example, if the valve is only partially opened, the gas feed rate may be insufficient to achieve the predetermined pressure threshold within the injection device's energy accumulator. This may result in liquid in the dose chamber being expelled at a pressure and velocity that is not sufficient to reach the target tissue depth. Alternatively, the pressure may be insufficient to unlock the pneumatic piston, thereby preventing liquid in the dose chamber from being expelled at all.

Third, because injection devices such as those described above include a power piston that is attached to and/or in constant contact with the medicine piston, more energy is required to move the pistons from the pre-injection position to the post-injection position. During the injection cycle, this limits the pressure profile of the injection because the power piston and medicine piston must both be moved throughout the injection cycle, instead of moving just one component (the power piston) during the preliminary phases of the injection cycle.

BRIEF SUMMARY OF THE INVENTION

The present invention is directed to an injection device and a method of using the same. The injection device includes an injection drive assembly, which itself includes pneumatic piston chamber, a dose chamber, a pneumatic piston slidably positioned in the pneumatic piston chamber and an injectate piston slidably positioned in the dose chamber.

In one aspect, the injection device of the present invention may include an injection drive assembly. The injection drive assembly includes the pneumatic piston chamber, the dose chamber, pneumatic piston slidably positioned in the pneumatic piston chamber, and the injectate piston slidably positioned in the dose chamber. The injection drive assembly is movable between a pre-injection position and a post-injection position. In certain aspects, the pneumatic piston and injectate pistons move independently of each other and are spaced apart from one another in certain positions within the injection device. The injection drive assembly is configured so that any energy resulting from an application of force to the injection drive assembly is instantaneously available for initiation of an injection cycle.

In another aspect, the injection device of the present invention may include separate respective resilient members for each of the pneumatic piston and the injectate piston. The pneumatic piston and the injectate piston are each movable between a pre-injection position and a post-injection position. Each respective resilient member is configured to position each of the pneumatic piston and the injectate piston in the pre-injection position.

In still another aspect, the injection device of the present invention may include a valve assembly that includes a valve. The valve is movable between a closed position and an open position. The valve is configured to provide pressurized fluid to the pneumatic piston chamber when the valve is in the open position. The rate of the movement of the valve between the closed position and the open position is independent of control by a user of the injection device.

In certain embodiments of the various aspects of the injection device of the present invention, the injection drive assembly is configured to make the energy resulting from an application of force to the injection drive assembly instantaneously available for the initiation of the injection cycle without first storing the energy as potential energy a) until the stored potential energy reaches a predetermined threshold and/or b) the stored potential energy is manually released.

Preferably, the injection drive assembly does not include an energy accumulator, including but not limited to a pressure accumulator such as a pressurized fluid accumulator. Accordingly, preferably, the pneumatic piston and the pneumatic piston chamber are not configured to operate as pressure accumulators.

Preferably, the injection drive assembly does not include a lock configured to retain the injection drive assembly in the pre-injection position. Preferably, the pneumatic piston is not held in the pre-injection position with a lock.

In other embodiments of the various aspects of the injection device of the present invention, the injection device includes separate respective resilient members for each of the pneumatic piston and the injectate piston that are configured to position each of the pneumatic piston and the injectate piston in the pre-injection position.

Preferably, the pneumatic piston and the injectate piston are not directly or indirectly attached to one another.

Preferably, when the injection drive assembly is in the pre-injection position, the pneumatic piston and the injectate piston are spaced apart from one another.

Preferably, the injection drive assembly is configured so that the energy resulting from the application of the force to the injection drive assembly is immediately available to move the pneumatic piston through a space between the pneumatic piston and injectate piston. More preferably, the injection drive assembly is configured so that the application of force to the injection drive assembly and a movement of the pneumatic piston generates kinetic energy sufficient to force the injectate piston forward.

Preferably, the pneumatic piston and the injectate piston are each in their most proximal positions when the injection drive assembly is in the pre-injection position. Preferably, the pneumatic piston and the injectate piston are each in their most distal positions when the injection drive assembly is in the post-injection position.

Preferably, each resilient member is a spring. Preferably, the force is supplied by a pressurized fluid. More preferably, the pressurized fluid is pressurized gas, pressurized fluid, and combinations thereof.

In still other embodiments of the various aspects of the injection device of the present invention, the injection device includes a valve assembly. The valve assembly includes a valve that is movable between a closed position and an open position and that is configured to provide pressurized fluid to the injection drive assembly when the valve is in the open position. A rate of a movement of the valve between the closed position and the open position is independent of control by a user of the injection device.

Preferably, the valve assembly further includes a valve switch resilient member and a valve switch. The valve switch resilient member is operable to move the valve switch from a position in which the valve is closed to a position in which the valve is open. Preferably, the valve switch resilient member is a spring. More preferably, the valve assembly further includes a valve switch latch that is configured to releasably retain the valve switch in a position in which the valve is closed.

Preferably, the injection device further includes a pneumatic piston chamber resilient member that is movable between a pre-actuation position and an actuation position. The pneumatic piston chamber resilient member is configured to position the pneumatic piston chamber in the pre-actuation position. Preferably, the valve switch resilient member is configured to be actuated via a movement of the pneumatic piston chamber to the actuation position. Preferably, the pneumatic piston chamber resilient member is a spring.

In another aspect, the present invention is directed to a method of using the injection device of the various aspects of the invention. The method includes the step of applying force to the injection drive assembly. The energy resulting from the application of the force to the injection drive assembly is instantaneously available for an initiation of an injection cycle. Preferably, the energy resulting from the application of the force to the injection drive assembly is instantaneously available for an injection cycle without first storing the energy as potential energy until a) the stored potential energy reaches a predetermined threshold and/or b) the stored potential energy is manually released.

Preferably, the method further includes the following additional steps: applying a first force to the injection drive assembly in the pre-injection position. The first force is sufficient to exceed a second force applied by the respective resilient member for the pneumatic piston. The first force forces a distal movement of the pneumatic piston. The distal movement of the pneumatic piston causes the pneumatic piston to contact the injectate piston, thereby applying a third force to the injectate piston. The third force is sufficient to exceed a fourth force applied by the respective resilient member for the injectate piston. The third force forces a distal movement of the injectate piston. The injection drive assembly is moved to the post-injection position, thereby forcing an injectate stored in the dose chamber out of the dose chamber. The third force is generated by the first force and kinetic energy generated from the movement of the pneumatic piston. The kinetic energy is dependent upon a length of a space between the pneumatic piston and the injectate piston. Preferably, the first force is supplied by a pressurized fluid. More preferably, the pressurized fluid is pressurized gas, pressurized liquid, or combinations thereof.

Preferably, the method further includes the following additional steps: providing a pressurized fluid to the valve, and moving the valve to the open position. The rate of the movement of the valve between the closed position and the open position is independent of control by the user of the injection device. More preferably, the method further includes the following additional steps: providing a pressurized fluid to the valve, and moving the pneumatic piston chamber from the pre-actuation position to the actuation position. The movement of the pneumatic piston chamber to the actuation position causes the actuation of the valve switch resilient member. Upon actuation, the valve switch resilient member causes the valve switch to move the valve from the closed position to the open position. once the valve is in the open position, the valve provides pressurized fluid to the pneumatic piston chamber. Preferably, the pressurized fluid is pressurized gas, pressurized liquid, or combinations thereof.

DETAILED DESCRIPTION OF PREFERRED EMBODIMENT

The present invention is directed to an injection device and a method of using the same. The injection device includes a pneumatic piston chamber, a dose chamber, a pneumatic piston slidably positioned in the pneumatic piston chamber and an injectate piston slidably positioned in the dose chamber. The injection device of the present invention can be utilized to inject animals and humans.

In one aspect, the injection device of the present invention may include an injection drive assembly. The injection drive assembly includes the pneumatic piston chamber, the dose chamber, pneumatic piston slidably positioned in the pneumatic piston chamber, and the injectate piston slidably positioned in the dose chamber. The injection drive assembly is movable between a pre-injection position and a post-injection position. In certain aspects, the pneumatic piston and injectate pistons move independently of each other and are spaced apart from one another in certain positions within the injection device. The injection drive assembly is configured so that any energy resulting from an application of force to the injection drive assembly is instantaneously available for initiation of an injection cycle.

In another aspect, the injection device of the present invention may include separate respective resilient members for each of the pneumatic piston and the injectate piston. The pneumatic piston and the injectate piston are each movable between a pre-injection position and a post-injection position. Each respective resilient member is configured to position each of the pneumatic piston and the injectate piston in the pre-injection position.

In still another aspect, the injection device of the present invention may include a valve assembly that includes a valve. The valve is movable between a closed position and an open position. The valve is configured to provide pressurized fluid to the pneumatic piston chamber when the valve is in the open position. The rate of the movement of the valve between the closed position and the open position is independent of control by a user of the injection device.

Figure 1:
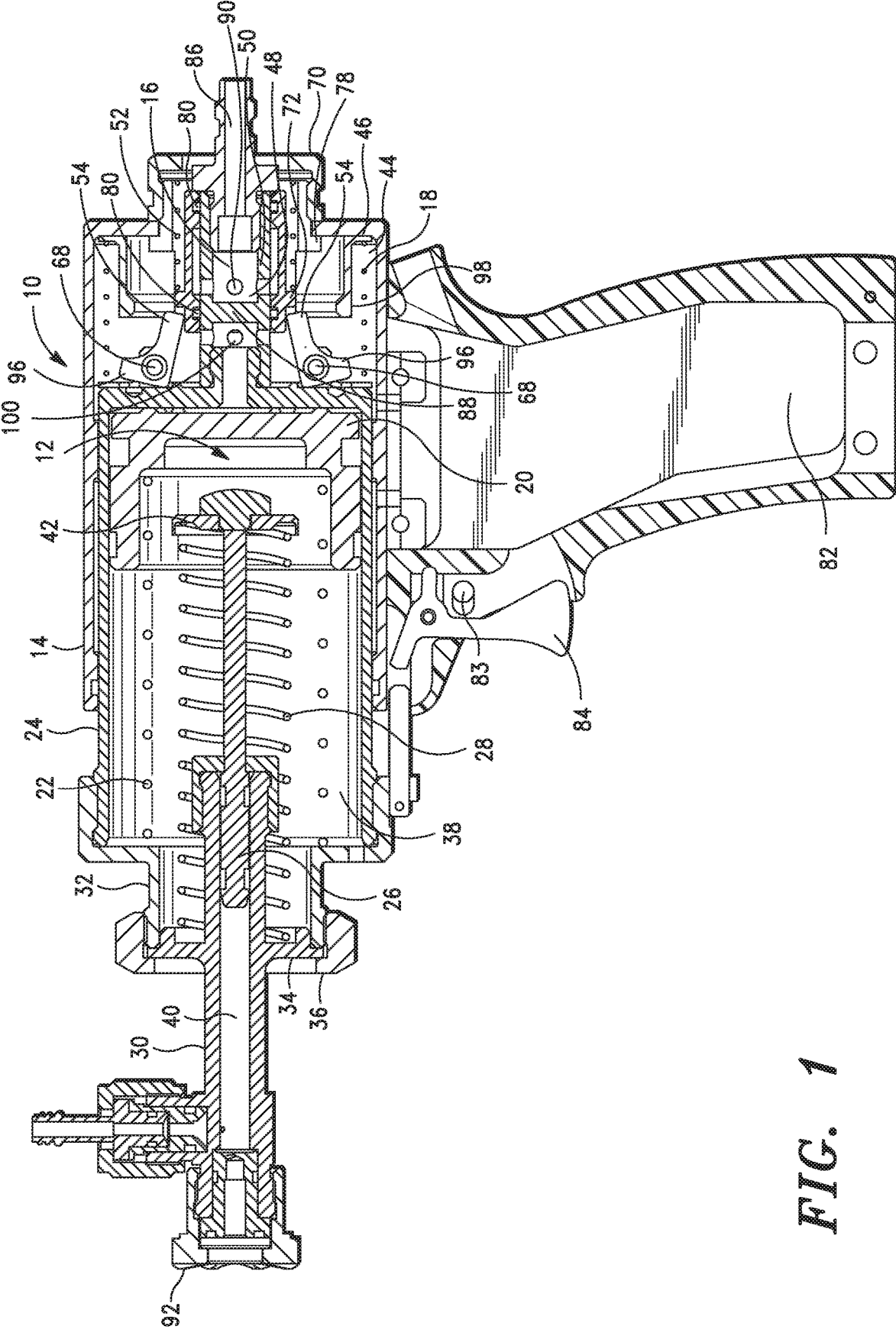
FIG. 1 is a cross-sectional view of an exemplary injection device of the present invention with the components of the injection drive assembly in the pre-injection position and the components of the valve is in the closed position.

The aforementioned aspects of the injection device of the present invention are described herein with respect to an exemplary embodiment of injection device 10 shown in FIG. 1. While injection device 10 includes all of the aforementioned aspects of the injection device of the present invention, it should be understood that the injection device of the present invention may include only some (as opposed to all) of those aspects. Further, while certain components of injection device 10 are described with respect to the figures, it will be understood that modifications may be made, for example, to the configuration and relationship of certain parts.

Referring to FIG. 1, injection device 10 is a needle-free injection device. However, it is within the scope of the present invention for the injection device to include a needle. Injection device 10 includes injection drive assembly 12, cylindrical outer housing 14, valve assembly 16, and actuation return spring 18. Injection drive assembly 12 includes pneumatic piston 20, pneumatic piston return spring 22, pneumatic piston chamber 24, injectate piston 26, injectate piston return spring 28, dose chamber 30, and dose chamber mount 32. The components of injection device 10 and injection drive assembly 12 are movable between the pre-injection position shown in FIG. 1 and the post-injection position shown in FIG. 2. The components of injection drive assembly 12 are generally cylindrical and are in axial alignment with one another and with actuation return spring 18 and outer housing 14. Dose chamber mount 32 is attached to a distal end of pneumatic piston chamber 24, and cylindrical dose chamber mounting flange 34 of dose chamber 30 is removably attached to a distal end of dose chamber mount 32 with dose chamber nut 36. Pneumatic piston 20 is slidably positioned within pneumatic piston chamber cavity 38, which is defined by pneumatic piston chamber 24 and dose chamber mount 32. A distal portion of injectate piston 26 is slidably positioned in dose chamber cavity 40, which is defined by dose chamber 30, and a proximal portion of injectate piston 26 and spring plate 42 attached thereto are positioned within pneumatic piston chamber cavity 38. Pneumatic piston chamber 24 is slidably positioned within an outer housing internal cavity 44 which is defined by outer housing 14. Actuation return spring 18 is also positioned within the outer housing internal cavity 44 between a proximal end of pneumatic piston chamber 24 and a proximal end wall 46 of outer housing 14.

Referring to FIG. 1, pneumatic piston return spring 22 and injectate piston return spring 28 are each resilient members that are configured to position each respective pneumatic piston and injectate piston in the pre-injection position. As described herein, pneumatic piston return spring 22 and injectate piston return spring 28 are each configured to return respective pneumatic piston 20 and injectate piston 26 from the post-injection position shown in FIG. 2 to the pre-injection position shown in FIG. 1. Pneumatic piston 20 and injectate piston 26 are separate components, are not directly or indirectly attached to one another, and are able to move independently of one another. Additionally, while pneumatic piston 20 and injectate piston 26 may abuttingly contact one another (for example, in the post-injection position), they do not abuttingly contact one another in all positions (for example, in the pre-injection position).

Returning to FIG. 1, pneumatic piston 20 and injectate piston 26 are each in their most proximal positions and are spaced apart from one another. As described herein, the spacing between pneumatic piston 20 and injectate piston 26 in the pre-injection position is important and affects the overall performance of the injection device 10. Shortly after the initiation of the injection cycle, this spacing allows the pneumatic piston 20 to move independently and to therefore build up kinetic energy before engaging with the proximal end of injectate piston 26. Thus, the distance between pneumatic piston 20 and injectate piston 26 in the pre-injection position determines how much kinetic energy the pneumatic piston 20 will accumulate prior to engaging the injectate piston 26. Accordingly, the spacing between pneumatic piston 20 and injectate piston 26 is directly correlated with the ability of the liquid expelled by injection device 10 to penetrate the skin of the animal or human. Therefore, by increasing the spacing between pneumatic piston 20 and injectate piston 26, the liquid expelled by injection device 10 can penetrate thicker tissues. Conversely, by decreasing the spacing between pneumatic piston 20 and injectate piston 26, the injection device 10 can be optimized to inject thinner tissues.

Referring still to FIG. 1, a proximal end of pneumatic piston return spring 22 is in abutting contact with pneumatic piston 20, and a distal end of pneumatic piston return spring 22 is in abutting contact with dose chamber mount 32. Pneumatic piston return spring 22 exerts force sufficient to position pneumatic piston 20 in the pre-injection position. A proximal end of pneumatic piston 20 is positioned against a proximal end of pneumatic piston chamber 24. A proximal end of injectate piston return spring 28 is in abutting contact with a distal end of spring plate 42, and a distal end of injectate piston return spring 28 is in abutting contact with dose chamber mounting flange 34. Injectate piston return spring 28 exerts force sufficient to position injectate piston 26 in the pre-injection position. A proximal end of actuation return spring 18 is in abutting contact with a proximal end wall 46 of outer housing 14, and a distal end of actuation return spring 18 is in abutting contact with a proximal end of pneumatic piston chamber 24. Actuation return spring exerts force sufficient to position pneumatic piston chamber 24 in the position shown. Pneumatic piston return spring 22, injectate piston return spring 28, and actuation return spring 18 each operate independently of one another to position respective pneumatic piston 20, injectate piston 26, and pneumatic piston chamber 24 in the positions shown in FIG. 1. Although actuation return spring 18, pneumatic piston return spring 22, and injectate piston return spring 28 are each springs, any suitable resilient members that are configured to position these components in the pre-injection position are within the scope of the present invention.

Figure 2:
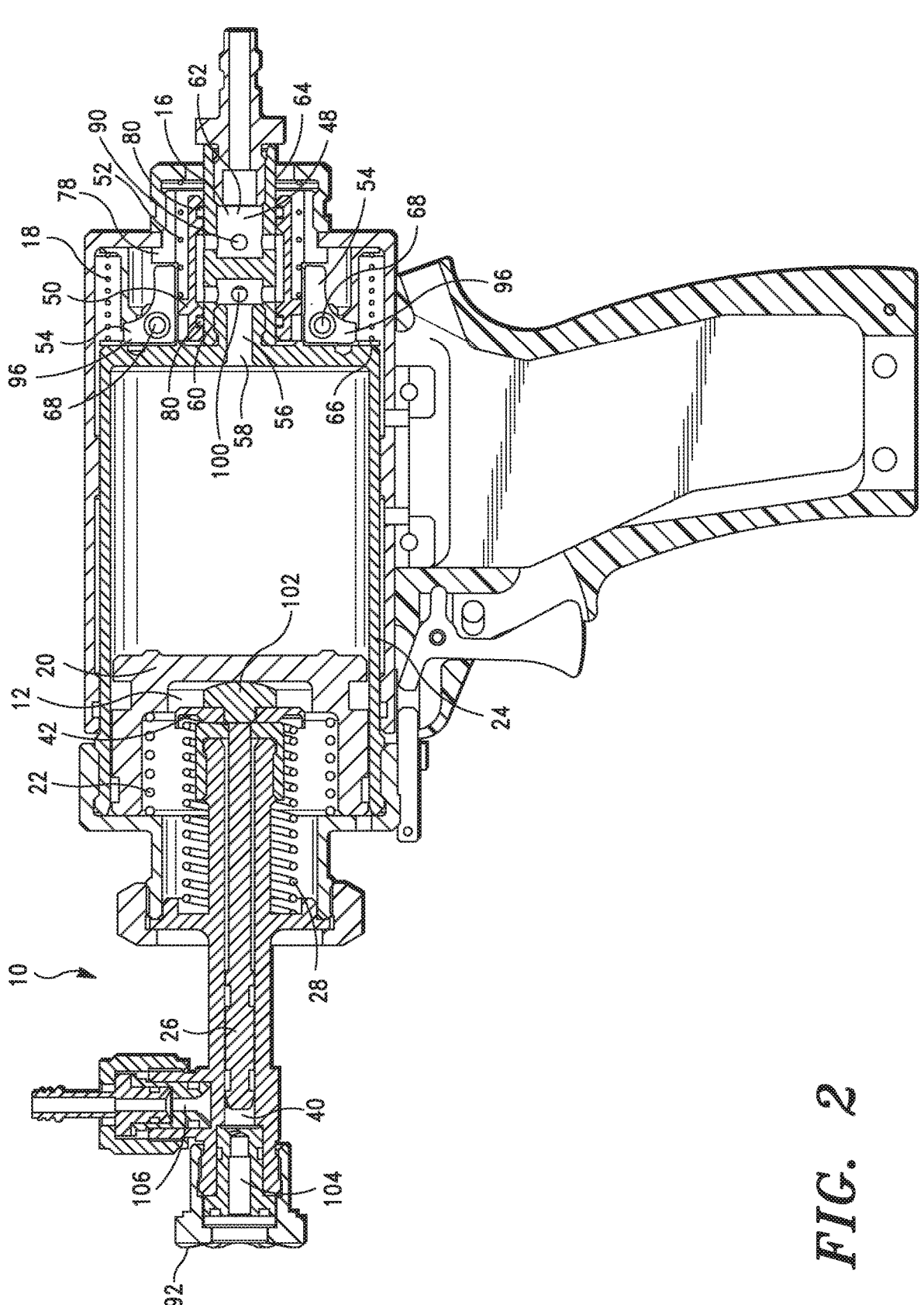
FIG. 2 is a cross-sectional view of the injection device of FIG. 1 in which the components of the injection drive assembly are in the post-injection position and the valve is in the open position.
Figure 3:
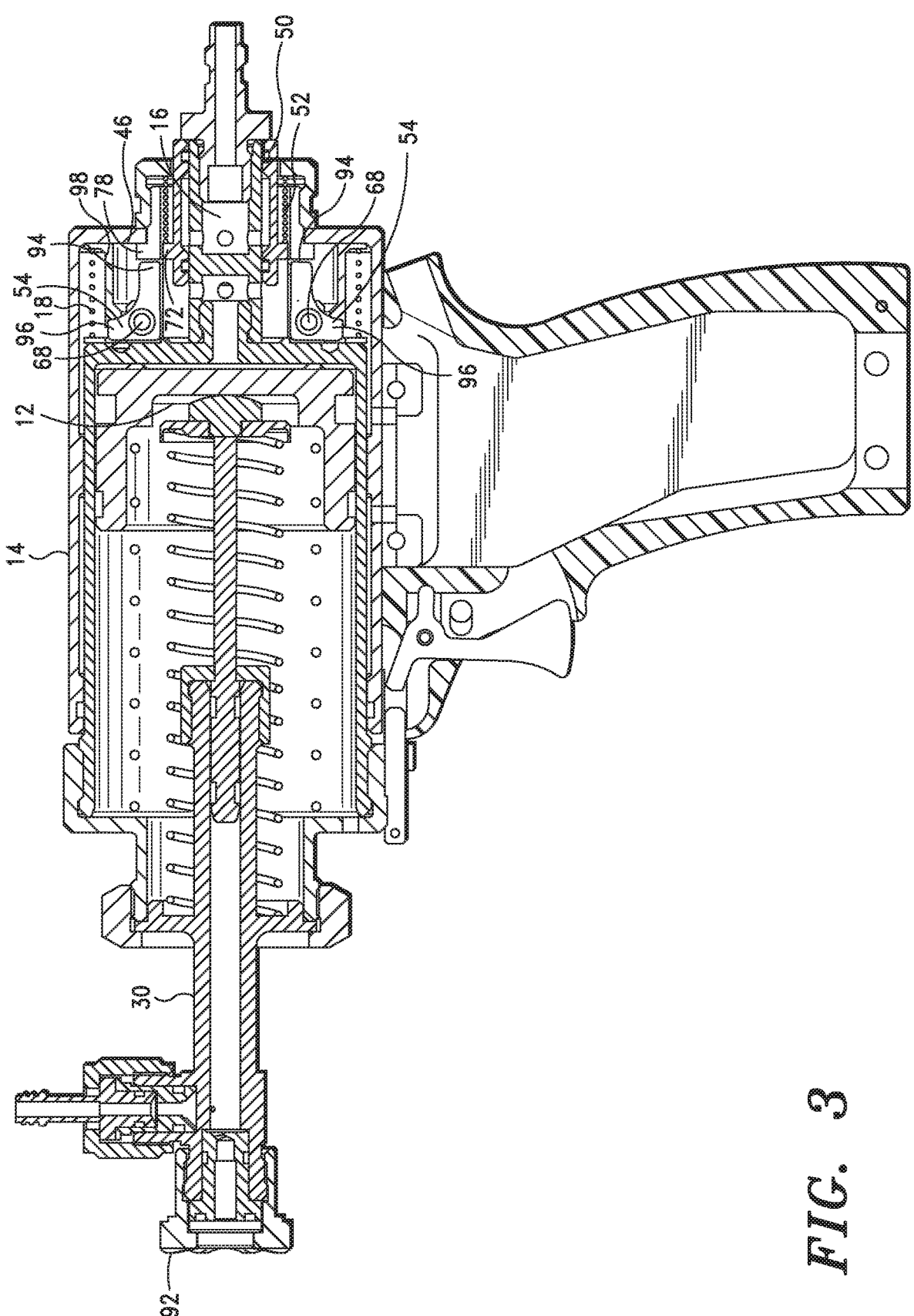
FIG. 3 is a cross-sectional view of the injection device of FIG. 1 in which the actuation return spring and the valve spring are fully compressed or cocked, the injection drive assembly is in the pre-injection position, and the valve is in the closed position.

The resilient members, such as the springs of FIGS. 1-3 provide sufficient force to position their respective components in a desired position prior to initiation of injection. However, they are unlike the locks of the prior art, in that minimal force is required from the resilient members to move and retain the respective components in position because there is no accumulated potential energy against which the resilient members are acting. This is important because, as discussed in more detail below, the force provided by the resilient members can be easily overcome immediately by a force applied in the opposing direction during the injection cycle. In addition, unlike the energy accumulators of the prior art, the force exerted by the resilient members upon the injection drive assembly is in a direction opposite to movement of the injection drive assembly at the initiation of the injection cycle. As a result, any potential energy in the resilient members is generated during, not prior to, the injection cycle and is released at the end of the injection cycle. Such potential energy is never made available prior to the initiation of the injection cycle in order to initiate the injection cycle.

The movement of injection drive assembly 12 between the pre-injection position shown in FIG. 1 and the post-injection position shown in FIG. 2 is effectuated by the application of force to injection drive assembly 12. As shown, injection device 10 is configured such that the force is provided by a pressurized gas (not shown) that is supplied to injection drive assembly 12 via valve assembly 16 when valve 48 is in the open position. Other suitable pressurized fluids include pressurized liquids or combinations of one or more pressurized gases and one or more pressurized fluids. Alternatively, the force supplied to injection drive assembly 12 may be provided by any suitable mechanism that is configured to force injection drive assembly between the pre-injection position and the post-injection position.

As described herein, injection drive assembly 12 is configured so that any energy resulting from an application of force to injection drive assembly 12 is instantaneously available for an initiation of an injection cycle. As noted above, this occurs in part because of the minimal force exerted by the resilient members and in part because power piston 20 is spaced apart from injectate piston 26 in the pre-injection position. Additionally, injection drive assembly 12 does not include one or more components that store the energy as potential energy prior to the initiation of the injection cycle until the stored potential energy either reaches a predetermined threshold or is manually released prior to making the energy available for the initiation of an injection cycle. As such, injection drive assembly 12 does not include an energy or pressure accumulator, none of its components (including pneumatic piston 20, pneumatic piston chamber 24, pneumatic piston return spring 22, injectate piston return spring 28, injectate piston 26 and injectate piston return spring 28) function as energy or pressure accumulators, and injection drive assembly 12 does not include a lock configured to counteract the potential energy to retain injection drive assembly 12 or any components thereof in the pre-injection position. For example, injection drive assembly 12 does not include a lock such as ball lock assembly (for example, as disclosed in the '054 Patent), a magnet, or a valve under pressure exerted by the potential energy prior to initiation of the injection cycle. Injection drive assembly 12 also does not include a spring under pressure exerted by the potential energy prior to the initiation of the injection cycle. As a result, injection drive assembly 12 and injection device 10 are less prone to wear and tear and to part failure.

Referring to FIG. 2, one aspect of the invention is directed to valve assembly 16 depicted therein. Valve assembly 16 includes cylindrical slide valve 48, cylindrical slide valve switch 50, slide valve switch spring 52, and a plurality of slide valve switch latches 54. Although only two slide valve switch latches 54 are shown, valve assembly 16 includes four valve switch latches 54. Although valve assembly 16 includes four valve switch latches 54, it is within the scope of the invention for valve assembly 16 to have more than four and as few as one valve switch latch 54. The components of valve assembly 16 are movable between the positions shown in FIG. 1 (in which valve 48 is closed) and FIGS. 2 and 4 (in which valve 48 is open). As described herein, the rate of movement of valve 48 between the closed position and the open position is independent of control by a user of injection device 10.

Referring back to FIG. 2, a port 56 is defined by cylindrical inner port surface 58 and cylindrical outer port surface 60 and extends proximally from a center of a proximal end of pneumatic piston chamber 24. A distal portion of cylindrical inner valve surface 62 of valve 48 is attached to cylindrical outer port surface 60 of port 56. A cylindrical outer valve surface 64 of valve 48 is slidably positioned within valve switch 50. Valve switch latches 54 are pivotally mounted onto a proximal end of valve switch plate 66 with pins 68, and valve switch plate 66 is in turn attached to a proximal end of pneumatic piston chamber 24.

Figure 5:
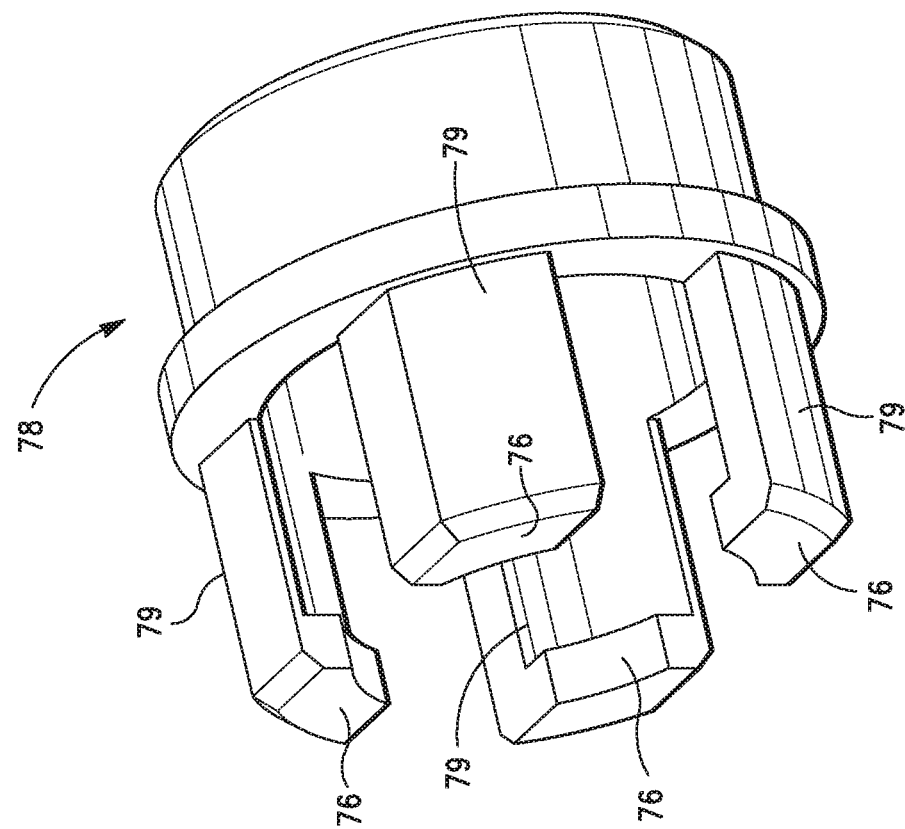
FIG. 5 is perspective view of retainer of the injection device of FIG. 1.

Referring back to FIG. 1, valve switch latches 54 are rotated about pins 68 laterally inward by latch springs (not shown) and toward a central longitudinal axis of valve 48. Valve switch spring 52 is positioned between and abuts a distal end of the outer housing end cap 70 and a proximal end of an outer cylindrical flange 72 positioned on a cylindrical outer valve switch surface 74 of valve switch 50. Valve switch spring 52 exerts a force against the proximal end of outer cylindrical flange 72 of valve switch 50, thereby causing a distal end of outer cylindrical flange 72 to abuttingly engage proximal portions of four retention flanges 76 of cylindrical retainer 78 (shown in FIG. 5), which is attached to proximal end wall 46 of outer housing 14. As a result, valve switch 50 is biased in the position shown. As shown in FIG. 5, retention flanges 76 are attached to retainer 78 via retention flange supports 79. Retention flange supports 79 are equally spaced apart about the perimeter of retainer 78. Referring to FIGS. 2 and 5, as described herein, this spacing allows for the unrestricted proximal and distal movement of the four valve switch latches 54 between corresponding adjacent retention flange supports 79. Referring to FIG. 2, as further described herein, valve switch spring 52 is configured to move valve switch 50 from the position in which valve 48 is closed to the position in which valve 48 is open. Although valve switch spring 52 is a spring, any suitable mechanisms that is configured to move valve switch 50 from the position in which valve 48 is closed to the position in which valve 48 is open are within the scope of the present invention. For example, a resilient member other than a spring may be utilized. As is also described herein, when valve 48 is in the closed position shown, rubber seals 80 of valve switch 50 create airtight seals that are configured to prevent any pressurized gas supplied to valve assembly 16 from entering injection drive assembly 12 or from escaping valve switch 50.

The injection cycle of injection device 10 and a method of using injection device 10 will now be described herein with respect to the exemplary embodiment depicted in the Figures. Prior to use, the components of injection device 10 are in the positions shown in FIG. 1. A user of injection device 10 may hold handle 82 of injection device 10. Safety (on/off) pin 83 is switched to the "on" position in order that the user may depress safety lever 84. The user then depresses safety lever 84 to enable the operation of injection device 10, and specifically, to enable the unrestricted movement of pneumatic piston chamber 24 within outer housing 14. Pressurized gas (not shown) is supplied at a constant pressure to valve assembly 16 via gas adapter 86. Because valve 48 is in the closed position, pressurized gas supplied to the valve assembly cannot enter the injection drive assembly 12 and cannot escape from valve switch 50. The pressurized gas is unable to enter the injection drive assembly because it cannot pass through valve barrier 88. Additionally, although the pressurized gas is able to exit valve 48 via valve bypass opening 90, rubber seals 80 of valve switch 50 create airtight seals that prevent the pressurized gas from exiting valve switch 50 and potentially entering the injection drive assembly.

Nozzle 92, which is attached to and in axial alignment with dose chamber 30, is positioned against a subject to be injected and is pressed against the subject, thereby compressing actuation return spring 18 and causing injection drive assembly 12 and valve assembly 16 to move proximally toward a proximal end of outer housing 14 until they reach the positions shown in FIG. 3. During this movement, proximal valve switch engaging portion 94 of valve switch latches 54 come into contact with and abuttingly engage a distal end of outer cylindrical flange 72 of valve switch 50, thereby causing valve switch to move proximally to the position shown in FIG. 3. Once injection drive assembly 12 and valve assembly 16 are in the position shown in FIG. 3, actuation return spring 18 and valve switch spring 52 are fully compressed or cocked. Once actuation return spring 18 and valve switch spring 52 are fully cocked, valve switch latches 54 rotate about pins 68 laterally outward to the positions shown in FIG. 3 as a result of the abutting contact of distal housing engaging structures 96 of valve switch latches 54 with a cylindrical latch engaging sidewall 98 attached to proximal end wall 46 of outer housing 14.

Figure 4:
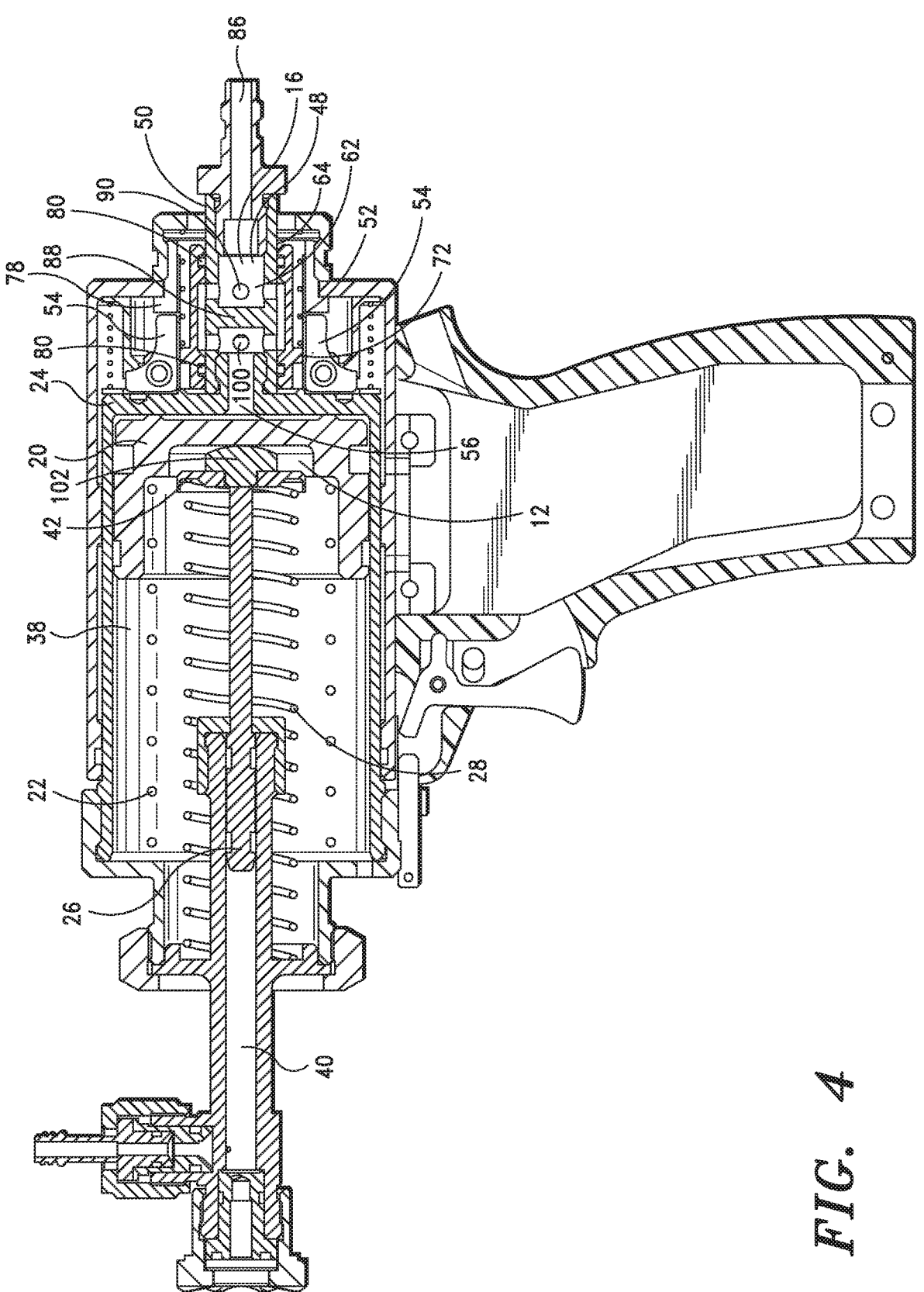
FIG. 4 is a cross-sectional view of the injection device of FIG. 1 in which the actuation return spring is fully compressed or cocked, the injection drive assembly is in the pre-injection position, and the valve is in the open position.

Once valve switch latches 54 no longer releasably retain valve switch 50, thereby restricting its distal movement, valve switch 50 moves rapidly distally from the position shown in FIG. 3 in which valve 48 is closed to the position shown in FIG. 4 in which valve 48 is open as a result of the decompression of valve switch spring 52. The distal movement of valve switch 50 is limited by the abutting engagement of a distal end of outer cylindrical flange 72 of valve switch 50 with the proximal portions of four retention walls 76 of retainer 78 (shown in FIG. 5). The rate of movement of valve 48 between the closed position shown in FIG. 3 and the open position shown in FIG. 4 is independent of control by a user of injection device 10; in other words, a user of injection device 10 cannot alter or manipulate the rate of movement of valve switch 50. For example, the rate at which a user causes injection drive assembly 12 and valve assembly 16 to move from the positions shown in FIG. 1 to the positions shown in FIG. 3 has no impact on the rate of movement of valve 48 from the closed to the open position.

It should be understood that valve switch spring 52 could be configured to be fully cocked other than as shown and described herein. For example, valve switch spring 52 could be configured to be manually cocked and released by a user. In such an embodiment, pneumatic piston chamber 24 need not necessarily be slidably positioned within outer housing 14 such that the movement of pneumatic piston chamber 24 would not be necessary to actuate valve switch spring 52, and injection device 10 need not necessarily include actuation return spring 18.

As valve switch 50 is moved to the position in which valve 48 is open shown in FIG. 4, pressurized gas (not shown) supplied via gas adapter 86 to valve assembly 16 is immediately released to injection drive assembly 12 through port 56 via valve 48. More specifically, pressurized gas is immediately supplied to a portion of pneumatic piston chamber 24 proximal to pneumatic piston 20 where the pressurized gas is instantaneously available for the initiation of the injection cycle. The pressurized gas enters a proximal portion of valve 48 from gas adapter 86. Once the pressurized gas is in a proximal portion of valve 48, it exits valve 48 via valve bypass opening 90 (which extends between inner valve surface 62 and outer valve surface 64) and re-enters a distal portion of valve 48 via valve exhaust opening 100 (which also extends between inner valve surface 62 and outer valve surface 64), thereby circumventing valve barrier 88. Because valve bypass opening 90 and valve exhaust opening 100 are each positioned between rubber seals 80 of valve switch 50, pressurized gas cannot escape valve switch 50, and all of the pressurized gas is directed to pneumatic piston chamber cavity 38.

The pressurized gas is provided to pneumatic piston chamber cavity 38 at a high feed rate due to the rapid movement of valve switch 50 from the position in which valve 48 is closed to the position in which valve is open. Once the pressurized gas enters pneumatic piston chamber cavity 38, it exerts a force against a proximal end of pneumatic piston 20 sufficient to exceed the limited force applied by pneumatic piston return spring 22 against a distal end of pneumatic piston 20. As a result, pneumatic piston 20 rapidly moves in a distal direction from the position shown in FIG. 4 to the post-injection position shown in FIG. 2, resulting in the compression of pneumatic piston return spring 22 as shown in FIG. 2. Initially, the acceleration of pneumatic piston 20 is unaffected by either injectate piston 26 or the dose (not shown) contained in dose chamber cavity 40 because pneumatic piston 20 is spaced apart from injectate piston 26 and is not connected either directly or indirectly to injectate piston 26. In other words, initially, neither injectate piston 26 nor the dose (not shown) present in dose chamber cavity 40 create any resistance to the distal movement and acceleration of pneumatic piston 20.

As pneumatic piston 20 moves distally, it generates kinetic energy, and pneumatic piston 20 strikes a proximal bulbous end 102 of injectate piston 26, thereby transferring some of its kinetic energy to injectate piston 26. The force applied by pneumatic piston 20 to injectate piston 26 is sufficient to exceed the limited force applied by injectate piston return spring 28 to a distal end of spring plate 42, and as a result, injectate piston 26 is forced to rapidly move distally, thereby compressing injectate piston return spring 28. The rapid distal movement of injectate piston 26 and pneumatic piston 20 results in a rapid spike of the hydraulic pressure of a dose (not shown) contained within dose chamber cavity 40, and the distal movement of injectate piston 26 to the position shown in FIG. 2 causes the dose to be expelled through outlet valve 104 and nozzle 92 and into the subject. Inlet valve 106, which is configured to allow liquid (not shown) to be drawn into dose chamber cavity 40, is also configured to prevent pressurized liquid within dose chamber cavity 40 from escaping through inlet valve 106.

As mentioned above, pneumatic piston return spring 22 and injectate piston return spring 28 are not energy accumulators. This is because, while these components do function to position respective pneumatic piston 20 and injectate piston 26 in the pre-injection position and must be compressed during the injection cycle in order to move injection drive assembly 12 to the post-injection position, they do not store energy as potential energy prior to the initiation of the injection cycle, until the stored potential energy either reaches a predetermined threshold or is manually released, prior to making the energy available for the initiation of an injection cycle. Instead, the energy supplied to injection drive assembly 12 to initiate the injection is supplied from the opposite direction and is immediately available to initiate an injection cycle.

Once the injection is complete and injection drive assembly 12 is in the post-injection position shown in FIG. 2, pneumatic piston 20 and injectate piston 26 are each in their most distal positions, and pneumatic piston 20 is in abutting contact with bulbous end 102 of injectate piston 26. Pneumatic piston return spring 22, injectate piston return spring 28, and actuation return spring 18 are each fully compressed or cocked. Following the injection with injection device 10, nozzle 92 is moved away from a subject to be injected, which allows actuation return spring 18 to decompress, thereby forcing pneumatic piston chamber 24 to move distally and return to the pre-injection position shown in FIG. 1.

As pneumatic piston chamber 24 moves distally, valve 48 and valve switch latches 54, which are attached to pneumatic piston chamber 24 as described above, also move distally. As a result, distal housing engaging structures 96 of valve switch latches 54 move out of abutting contact with cylindrical latch engaging sidewall, thereby allowing valve switch latches to rotate about pins 68 laterally inward to the positions shown. Additionally, valve 48 returns to the closed position, thereby causing valve exhaust opening 100 to move out of alignment with valve switch 50 such that valve exhaust opening 100 is not positioned between rubber seals 80 of valve switch 50. In this position, residual pressurized gas contained within pneumatic piston chamber 24 may escape through valve exhaust opening 100 as pneumatic piston return spring 22 decompresses and forces pneumatic piston 20 to move proximally.

As pneumatic piston 20 moves out of abutting contact with injectate piston 26, injectate piston return spring 28 decompresses and forces injectate piston 26 to move proximally and return to the pre-injection position, at which point all components of injection drive assembly 12 are in the pre-injection position shown in FIG. 1. The proximal movement of injectate piston 26 creates negative pressure within dose chamber 30, which in turn causes liquid (not shown) to be drawn into dose chamber cavity 40 from inlet valve 106. As a result, injection device 10 is now ready to complete another injection cycle. Although only one valve bypass opening 90 and one valve exhaust opening 100 are shown, valve 48 includes two valve bypass openings 90 and two valve exhaust openings 100. Although valve 48 includes two valve bypass openings 90, valve 48 may alternatively have only one or more than two valve bypass openings 90. Similarly, although valve includes two valve exhaust openings 100, valve 48 may alternatively have only one or more than two valve exhaust openings 100. Further, it should be understood that although the operation of injection device 10 has been described with respect to one embodiment of valve assembly 16 in combination with certain other valves and openings, other types of valves and exhausts can be used to control gas flow into and out injection device 10. Any valve assembly that is configured to provide pressurized gas to injection drive assembly 12 in order to initiate an injection cycle and to allow pressurized gas to escape injection drive assembly 12 as pneumatic piston 20 and injectate piston 26 return to the pre-injection position is within the scope of the invention. Further, in certain other embodiments the force may be provided in such a manner that a valve is not present.

From the foregoing it will be seen that this invention is one well adapted to attain all ends and objectives herein-above set forth, together with the other advantages which are obvious and which are inherent to the invention.

Since many possible embodiments may be made of the invention without departing from the scope thereof, it is to be understood that all matters herein set forth or shown in the accompanying drawings are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

I claim:

1. An injection device comprising:
an injection drive assembly, wherein the injection drive assembly comprises:
a pneumatic piston chamber;
a dose chamber;
a pneumatic piston slidably positioned in the pneumatic piston chamber;
an injectate piston slidably positioned in the dose chamber; and
separate respective resilient members for each of the pneumatic piston and the injectate piston, wherein each respective resilient member is configured to position of each the pneumatic piston and the injectate piston in a pre-injection position;
wherein the injection drive assembly is movable between the pre-injection position and a post-injection position; and
wherein the injection drive assembly is configured so that any energy resulting from an application of force to the injection drive assembly is instantaneously available for an initiation of an injection cycle.

2. The injection device of claim 1, wherein the injection drive assembly is configured to make the energy resulting from an application of force to the injection drive assembly instantaneously available for the initiation of the injection cycle without first storing the energy as potential energy until the stored potential energy reaches a predetermined threshold.

3. The injection device of claim 1, wherein the injection drive assembly is configured to make the energy resulting from an application of force to the injection drive assembly instantaneously available for the initiation of the injection cycle without first storing the energy as potential energy until the stored potential energy is manually released.

4. The injection device of claim 1, wherein the injection drive assembly does not include an energy accumulator.

5. The injection device of claim 4, wherein the energy accumulator is a pressure accumulator.

6. The injection device of claim 5, wherein the pressure accumulator is a pressurized fluid accumulator.

7. The injection device of claim 5, wherein the pneumatic piston is not configured to operate as a pressure accumulator.

8. The injection device of claim 5, wherein the pneumatic piston chamber is not configured to operate as a pressure accumulator.

9. The injection device of claim 1, wherein the injection drive assembly does not include a lock configured to retain the injection drive assembly in the pre-injection position.

10. The injection device of claim 9, wherein the pneumatic piston is not held in the pre-injection position with the lock.

11. The injection device of claim 1, wherein the pneumatic piston and the injectate piston are not directly or indirectly attached to one another.

12. The injection device of claim 1, wherein when the injection drive assembly is in the pre-injection position, the pneumatic piston and the injectate piston are spaced apart from one another.

13. The injection device of claim 12, wherein the injection drive assembly is configured so that the energy resulting from the application of the force to the injection drive assembly is immediately available to move the pneumatic piston through a space between the pneumatic piston and injectate piston.

14. The injection device of claim 12, wherein the injection drive assembly is configured so that the application of force to the injection drive assembly and a movement of the pneumatic piston generates kinetic energy sufficient to force the injectate piston forward.

15. The injection device of claim 1, wherein the pneumatic piston and the injectate piston are each in their most proximal positions when the injection drive assembly is in the pre-injection position.

16. The injection device of claim 1, wherein the pneumatic piston and the injectate piston are each in their most distal positions when the injection drive assembly is in the post-injection position.

17. The injection device of claim 1, wherein each resilient member is a spring.

18. The injection device of claim 1, wherein the force is supplied by a pressurized fluid.

19. The injection device of claim 18, wherein the pressurized fluid is selected from the group consisting of pressurized gas, pressurized liquid, and combinations thereof.

20. An injection device comprising:
an injection drive assembly, wherein the injection drive assembly comprises:
a pneumatic piston chamber;
a dose chamber;
a pneumatic piston slidably positioned in the pneumatic piston chamber; and
an injectate piston slidably positioned in the dose chamber;
wherein the injection drive assembly comprises only one pneumatic piston slidably positioned in the pneumatic piston chamber;
wherein the injection drive assembly is movable between a pre-injection position and a post-injection position; and
wherein the injection drive assembly is configured so that any energy resulting from an application of force to the injection drive assembly is instantaneously available for an initiation of an injection cycle.

21. An injection device comprising:
an injection drive assembly, wherein the injection drive assembly comprises:
a pneumatic piston chamber;
a dose chamber;
a pneumatic piston slidably positioned in the pneumatic piston chamber; and
an injectate piston slidably positioned in the dose chamber;
wherein the injection drive assembly is movable between a pre-injection position and a post-injection position;

US 12,629,475 B2

17 wherein the injection drive assembly is configured so that
any energy resulting from an application of force to the
injection drive assembly is instantaneously available
for an initiation of an injection cycle;
wherein the pneumatic piston and the injectate piston are
not directly or indirectly attached to one another;
wherein when the injection drive assembly is in the
pre-injection position, the pneumatic piston and the
injectate piston are spaced apart from one another; and
wherein the pneumatic piston is configured to contact the
injectate piston when the pneumatic piston moves from
the pre-injection position to the post-injection position.

\* \* \* \* \*